(12) United States Patent
Vaz et al.

(10) Patent No.: US 8,845,660 B2
(45) Date of Patent: Sep. 30, 2014

(54) SURGICAL REPAIR ARTICLE BASED ON HPPE MATERIAL

(75) Inventors: Claudia Maria Vaz, Maastricht (NL); Gerardus Aben, Montfort (NL); Edith Elisabeth Van Den Bosch, Riemst (BE)

(73) Assignee: DSM IP Assets B.V., Heerlen (NL)

( * ) Notice: Subject to any disclaimer, the term of this patent is extended or adjusted under 35 U.S.C. 154(b) by 0 days.

(21) Appl. No.: 13/389,121

(22) PCT Filed: Aug. 5, 2010

(86) PCT No.: PCT/EP2010/061398
§ 371 (c)(1),
(2), (4) Date: Jul. 23, 2012

(87) PCT Pub. No.: WO2011/015619
PCT Pub. Date: Feb. 10, 2011

(65) Prior Publication Data
US 2012/0277771 A1 Nov. 1, 2012

(30) Foreign Application Priority Data

Aug. 6, 2009 (EP) .................... 09167348
Nov. 13, 2009 (EP) .................... 09175938

(51) Int. Cl.
*A61B 17/03* (2006.01)
*B05D 7/00* (2006.01)
*A61L 17/10* (2006.01)
*A61L 17/14* (2006.01)
*A61L 17/00* (2006.01)
*C08L 23/06* (2006.01)

(52) U.S. Cl.
CPC ............. *A61L 17/145* (2013.01); *A61L 17/10* (2013.01); *A61L 2300/604* (2013.01); *A61L 2300/404* (2013.01); *A61L 17/005* (2013.01); *D10B 2509/04* (2013.01); *A61L 2300/606* (2013.01); *C08L 23/06* (2013.01); *A61L 2300/414* (2013.01)
USPC ............................ 606/151; 606/228; 427/2.1

(58) Field of Classification Search
None
See application file for complete search history.

(56) References Cited

U.S. PATENT DOCUMENTS

| | | | |
|---|---|---|---|
| 5,312,437 A * | 5/1994 | Hermes et al. ................. | 606/230 |
| 6,403,666 B1 | 6/2002 | Nakayama et al. | |
| 6,482,444 B1 * | 11/2002 | Bellantone et al. ............ | 424/618 |
| 2006/0155329 A1 | 7/2006 | Grafton et al. | |
| 2006/0177489 A1* | 8/2006 | Massouda et al. ............. | 424/443 |
| 2007/0134305 A1* | 6/2007 | Zilberman ..................... | 424/443 |
| 2009/0048628 A1 | 2/2009 | Marissen | |

FOREIGN PATENT DOCUMENTS

| | | |
|---|---|---|
| CN | 101243984 | 8/2008 |
| CN | 101336116 | 12/2008 |
| EP | 1 897 500 | 3/2008 |
| JP | 2009-525124 | 7/2009 |
| WO | 2007/092043 | 8/2007 |
| WO | WO 2007/092043 | 8/2007 |
| WO | 2009/013340 | 1/2009 |

OTHER PUBLICATIONS

International Search Report for PCT/EP2010/061398, mailed Jan. 20, 2011.
Written Opinion for PCT/EP2010/061398, mailed Jan. 20, 2011.

* cited by examiner

*Primary Examiner* — Kortney L Klinkel
*Assistant Examiner* — Ping Cao
(74) *Attorney, Agent, or Firm* — Nixon & Vanderhye P.C.

(57) ABSTRACT

The invention relates to a surgical repair article, comprising a structural member of high performance polyethylene (HPPE) filament(s). The invention also relates to a method of making such a surgical repair article, and to a kit of parts comprising the article. The surgical repair article comprises a structural member of high performance polyethylene (HPPE) filament (s), and a biodegradable coating applied to the surface of the structural member, wherein the coating comprises a sol/gel produced inorganic oxide and a biologically active compound incorporated therein. The article combines high tensile strength, biocompatibility and favorable bioactive compound delivery characteristics.

28 Claims, 3 Drawing Sheets

SURGICAL REPAIR ARTICLE BASED ON HPPE MATERIAL

This application is the U.S. national phase of International Application No. PCT/EP2010/061398 filed 5 Aug. 2010 which designated the U.S. and claims priority to EP Patent Application Nos. 09167348.3 filed 6 Aug. 2009 and 09175938.1 filed 13 Nov. 2009, the entire contents of each of which are hereby incorporated by reference.

The invention relates to a surgical repair article, comprising a structural member of high performance polyethylene (HPPE) filament(s). The invention also relates to a method of making such a surgical repair article, and to a kit of parts comprising the article.

Surgical repair articles like sutures have been made over time from a variety of materials, including flax, hair, cotton, silk, animal gut, and synthetic materials like polyesters, polyamides, and polyolefin's, such as polyethylene or polypropylene. EP 1293218 A1 for instance discloses an elongated suture for use as a surgical suture or ligament, which suture comprises a core of twisted strands of ultra-high molar mass polyethylene (UHMWPE) filaments, surrounded by a multifilament braided sheath also comprising UHMWPE filaments. EP 1293218 A1 discloses that the suture may be uncoated or coated with wax (beeswax, polyethylene wax, petroleum wax or others), silicone, silicone rubbers, PTFE, PBA, ethyl cellulose or other coatings to improve lubricity of the braid, knot security, or abrasion resistance, for example.

There is a need in the industry for a surgical repair article that effectively utilizes the high strength (tenacity) of HPPE monofilament or multi filaments but at the same time is able to offer controlled release of biologically active agents, preferably anti-microbial agents.

The object of the present invention is therefore to provide a surgical repair article comprising a structural member based on high performance polyethylene (HPPE) filament(s) that has high tensile strength, good flexibility and moreover is able to offer controlled release of biologically active agents.

This object is achieved according to the invention by providing a surgical repair article, comprising a structural member of high performance polyethylene filament(s), and a biodegradable coating applied to the surface of the structural member, wherein the coating comprises a sol/gel produced inorganic oxide and a biologically active compound incorporated therein.

By providing a bio-resorbable coating comprising a sol/gel produced inorganic oxide and a biologically active compound incorporated therein, a controlled release of the biologically active compound is achieved after implantation of the article in a living organism. By applying a coating onto the HPPE structural member that is bio-resorbable, this coating will within a given time frame degrade, and thereby will release at least a part of the biologically active agent. Release of the agent is substantially controlled by degradation of the coating, i.e. by its bio-resorbable properties, and does not rely solely on diffusion of the agent through the coating. After substantially complete degradation of the coating within a controllable time-frame, a structural member of HPPE filaments is left in the living organism, which member is biocompatible and therefore poses no problem to the living organism.

The desired property of controlled release of the agent requires that the coating preferably adheres well to the HPPE structural member. If not, parts of the coating could easily come loose from the member whereby the amount and release of the agent would be affected. From another perspective, the excellent mechanical properties of the structural member, such as its bending performance for instance, are used advantageously when handling the structural member. A suture of HPPE for instance is readily knotted and thereby retains its mechanical properties, resulting in a high knotting strength. During handling of such an article, the coating should preferably remain on the article to a large extent. It has turned out that the selected sol/gel coating provides a fairly strong bond with the surface of the structural member and/or the surface of the filament(s). This is surprising since HPPE is well known for its inertness and therefore difficult to bond to other materials. However, if was found that in obtaining a very strong bond between the sol/gel coating and the HPPE, pre-treatment of the HPPE was a major advantage. Various pre-treatments are possible and discussed elsewhere in the present specification.

It should be noted that inorganic oxides produced by a sol/gel process are known per se for use as a porous coating, for instance from WO 2007/092043A2. This document discloses the use of sol-gel compositions as drug reservoirs on implantable medical devices. However the disclosed compositions are not bio-resorbable, and release of the drugs is diffusion controlled. It is difficult therefore to control the rate of drug delivery, since release of the drug depends on a number of variables, such as porosity, interconnectivity of the pores, pore dimensions and distribution, and more.

The release mechanism of the repair article according to the invention is at least in part based on biodegradation of the coating, and more in particular its bio-resorbance. The term biodegradable is often used as a general definition for degradation in (contact with) living organisms. The terms bio-resorbable or bio-absorbable are often used to describe materials degradation in (contact with) the living organism, mostly for implanted biomaterials in living tissue describing a degradation mechanism mainly governed by dissolution in the body fluids or by a mechanism that is not exactly known.

BRIEF DESCRIPTION OF THE DRAWINGS

The invention will be explained more fully below with reference to exemplary embodiments as well as the drawings, in which.

DESCRIPTION OF THE DRAWINGS AND PREFERRED EMBODIMENTS

The surgical repair article according to the invention comprises a structural member containing HPPE monofilament or filaments, and preferably an elongated structural member of HPPE filament(s). Examples of suitable elongated structural members include a non-woven or woven or (hollow) braided construction of HPPE filaments or multifilament yarns, of tape- or ribbon-like appearance, substantially (hollow) cylindrical twisted or untwisted HPPE yarns, either monofilament or multifilament, optionally at least partly fused, and the like.

An elongated surgical repair article is understood to be an article for instance for use as a surgical suture for repairing body tissue, or for use as a cable, mesh, fabric, woven or non-woven sheet, tape, ribbon or band for repairing or retaining body parts like bones, the article having a substantially larger length dimension than its cross-sectional dimensions (width and thickness, or diameter). The repair article preferably comprises at least one elongated structural member, which is generally the load-bearing component and is made from high performance monofilament or filaments. High performance filaments have a high modulus, high strength, and may be melt spun or, preferably gel spun. High performance polyethylene filament(s) have a tensile strength exceeding 1.0 GPa. The article may further comprise an anchor and/or a needle for easy attachment, or a coating material to provide the article with certain surface properties.

A preferred embodiment of the article according to the invention comprises ultra-high molar mass polyethylene (UHMWPE) filament(s). Within the context of the present application ultra-high molar mass polyethylene (UHMWPE) is understood to be polyethylene with an intrinsic viscosity (IV, as determined according to method PTC-179 (Hercules Inc. Rev. Apr. 29, 1982) at 135° C. in decalin, with dissolution time of 16 hours, with anti-oxidant DBPC in an amount of 2 g/l solution, and the viscosity at different concentrations extrapolated to zero concentration) of above 5 dl/g. Particularly suitable for the filaments is UHMWPE with an intrinsic viscosity IV of between about 8 and 40 dl/g, more preferably between 10 and 30, or 12 and 28, or between 15 and 25 dl/g. These ranges represent an optimum in polymer processability and filament properties. Intrinsic viscosity is a measure for molar mass (also called molecular weight) that can more easily be determined than actual molar mass parameters like Mn and Mw. There are several empirical relations between IV and Mw, but such relation is highly dependent on molar mass distribution. Based on the equation $Mw=5.37\times10^4 [IV]^{1.37}$ (see EP 0504954 A1) an IV of 8 dl/g would be equivalent to Mw of about 930 kg/mol. Such HPPE is preferred due to the high strength of more than about 2.5 GPa, very low elongation at breakage and very high E-modulus obtainable by gelspinning. This leads to improved control to surgeons during use and the high modulus and low elongation at breakage prevents loosening of the coating during use.

Preferably, the UHMWPE is a linear polyethylene with less than one branch or side chain per 100 carbon atoms, and preferably less than one side chain per 300 carbon atoms, a branch usually containing at least 10 carbon atoms. The linear polyethylene may further contain up to 5 mol % of one or more comonomers, such as alkenes like propylene, butene, pentene, 4-methylpentene or octene.

In a preferred embodiment, the UHMWPE contains a small amount of relatively small groups as side chains, preferably a C1-C4 alkyl group. It is found that a filament from UHMWPE with a certain amount of such groups show reduced creep behaviour. Too large a side chain, or too high an amount of side chains, however, negatively affects the processing and especially the drawing behaviour of the filaments. For this reason, the UHMWPE preferably contains methyl or ethyl side chains, more preferably methyl side chains. The amount of side chains is preferably at least 0.3, 0.5, more preferably at least 1 per 1000 carbon atoms, and preferably at most 20, more preferably at most 10 per 1000 carbon atoms.

The UHMWPE can be a single polymer grade, but also a mixture of two or more different grades, e.g. differing in IV or molar mass distribution, and/or number of side chains.

The UHMWPE polymer may further contain usual amounts, generally less than 10 vol % of customary additives, such as anti-oxidants, thermal stabilizers, functional pigments, colorants, electromagnetic additives, radiopaque additives, nucleating agents, flow promoters, catalyst residues etc.; as long as these components are suitable for the use in a surgical article. The filament (or sheath) may also contain other polymers, preferably polyolefinic polymers, like other polyethylenes, polypropylenes, or their copolymers, including rubbery copolymers like EPDM, EPR, etc. The amount of such other polymer is always lower than the amount of UHMWPE in the filaments, and is preferably not more than 30% of the UHMWPE. Most preferably, the polymer consist substantially or completely of UHMWPE.

The structural elongated member contains a plurality of high-strength HPPE filaments, preferably UHMWPE filaments. Filaments are herein understood to be of indefinite length; or at least to have about the same length as the structural elongated member. Preferably, the tensile strength of the filaments is more than 1.5, 2.0 or even more than 3.0 GPa. Tensile strength, also simply strength, is determined on multifilament yarns as specified in ASTM D885M, using a nominal gauge length of the fibre of 500 mm, a crosshead speed of 50%/min and Instron 2714 clamps, type Fibre Grip D5618C. Higher strength of the filaments also results in higher strength of the surgical article.

The HPPE filaments in the member in the article according to the invention may have a filament linear density or titer varying between wide ranges. A suitable titer for the filaments is between about 0.2 and 20 dtex per filament, preferably about 0.3-10 dtex, or 0.4-5 dtex; since this results in a favourable combination of improved strength and high flexibility of the member and article.

Suitable HPPE and UHMWPE filaments can be made by a method generally referred to as gel spinning. Gel spinning of HPPE and UHMWPE is well known to the person skilled in the art; and described in numerous publications, including EP 0205960 A, EP 0213208 A1, U.S. Pat. No. 4,413,110, GB 2042414 A, EP 0200547 B1, EP 0472114 B1, WO 01/73173 A1, and Advanced Fiber Spinning Technology, Ed. T. Nakajima, Woodhead Publ. Ltd (1994), ISBN 1-855-73182-7, and references cited therein. Gel spinning is understood to include at least the steps of spinning at least one filament from a solution of ultra-high molecular weight polyethylene in a spin solvent; cooling the filament obtained to form a gel filament; removing at least partly the spin solvent from the gel filament; and drawing the filament in at least one drawing step before, during or after removing spin solvent. Suitable spin solvents include for example paraffins, mineral oil, kerosene or decalin. Spin solvent can be removed by evaporation, extraction, or by a combination of evaporation and extraction routes. The HPPE and UHMWPE filaments preferably contain less than 800 ppm of residual amounts of spin solvent, more preferably less than 250 ppm, even less than 100 ppm, and most preferably less than 20 ppm. The HPPE filaments may also be made by melt spinning, known per se.

The structural member may in addition to HPPE filaments also contain other filaments, but preferably not more than 40 mass % of the total amount of filaments, more preferably not more than 30, 20, or 10 mass %. In view of optimum strength of the member, the core preferably only contains high performance filaments, more preferably only HPPE filaments.

Another desirable property for the structural member would be the ability to offer controlled release of biologically active agents, such as for instance anti-microbial agents, to impart anti-microbial properties to the repair article. In a highly preferred embodiment, the article then acts as a temporary reservoir for the agents, which are released after implantation of the article in the human body.

A frequent problem occurs when trying to impart bioactivity to a material by modifying it, in that other desirable properties of the material, such as high strength for instance, may be affected. This is not acceptable. Also, release of the bioactive substance is often insufficient.

According to the present invention, the repair article is provided with a bio-resorbable coating applied to the surface of the structural member and/or the surface of the filament(s), wherein the coating comprises a sol/gel produced inorganic oxide.

A sol is a liquid solution containing a colloid suspension of a material of interest dissolved in an appropriate solvent. Condensation reactions between the dissolved precursor molecules result in macromolecular structures such as branched chains, forming within the sol. The size, growth rate and morphology of these structures depend on the kinetics of the reactions within the solvent, which in turn are determined by parameters such as solution concentration, amount of water present, the temperature and pH of the solvent, agitation of the solvent and other parameters. Given enough time, heating and/or pH, condensation reactions will lead to the aggregation of growing particles or chains until eventually, a gel is formed. The gel can be visualized as a very large number of cross-linked precursor molecules forming a continuous, macroscopic-scale, solid phase, which encloses a continuous liquid phase consisting of the remaining solution. In the final steps of the sol-gel process, the enclosed solvent is removed, generally by drying, and the precursor molecules cross-link (a process called aging) resulting in the desired porous solid.

Sol-gel synthesis of the inorganic oxide of the present invention offers the advantage of mild processing conditions (low temperature, low pressure, mild pH) that will not significantly impair the mechanical properties of the HPPE structural member. Also, a high level of control over the resulting structure, particularly as it pertains to porosity and bio-resorbable properties, is another advantage.

Porosity of the inorganic oxide coating can be controlled in a number of different ways. In the simplest sol-gel process, no special porogen is added to the sol and the porosity of the final solid coating is determined by the amount and type of precursor branching or aggregation before gelling. Average pore size, volume and surface area of porous sol-gel compositions increase with the size and type of the precursor molecules prior to the sol-gel processing.

Porosity of the inorganic oxide coating can also be manipulated by adding additional materials to the solvent during the sol-gel process. The incorporation of sacrificial porogens in the sol (particularly those that can be easily removed via heating or other methods) is generally viewed as an efficient method to obtain porous solids when using sol-gel processes. Sacrificial templates can also be used to create pores in inorganic materials formed using sol-gel processes, such as those using amphiphilic molecules capable of self-assembling in solution.

The sol/gel produced coatings may be porous. A preferred embodiment of the article however comprises a sol/gel produced coating with a relatively low porosity, preferably of less than 30 vol. % pores, more preferably of less than 15 vol. % of pores, and most preferably of less than 10 vol. % of pores, relative to the total volume of the sol/gel produced coating.

The inorganic oxide is preferably selected from the group consisting of silicon oxides, aluminium oxides, titanium oxides and zirconium oxides. Most preferred is an article wherein the inorganic oxide is a silicon oxide. This type of inorganic oxide adheres well to the structural member of HHPE filaments, and moreover does not substantially affect desired properties of high strength and flexibility. The coating composition can also be a mesoporous inorganic oxide. Mesoporous inorganic oxides can be obtained using a sacrificial pore-generating template component. Mesoporous inorganic oxides can comprise substantially continuous interconnected channels.

In certain embodiments of the present invention, the inorganic oxide can be compounded with an agent that modifies a characteristic of the oxide. Suitable compounds are selected from the group consisting of hydrophobic agents, charge modifying agents, biocompatible agents, mechanical property enhancers, agents modifying bioactive material affinity, storage capacity and combinations thereof. In one embodiment, the modifying agent is an organically modified silane.

According to the invention, one or more biologically active agents are incorporated into the coating material before, during or after the coating is applied to the surface of the structural member. The biologically active agent can be any organic, inorganic or living agent that is biologically active. Suitable biologically active agents include a protein, a polypeptide, a polysaccharide (e.g. heparin), an oligosaccharide, a mono- or disaccharide, an organic compound, an organometallic compound or an inorganic compound. It can also be a living or dead cell, bacterium, a virus or a part thereof. It can be a biologically active molecule such as a hormone, a growth factor, a growth factor producing virus, a growth factor inhibitor, a growth factor receptor, or a complete or partial functional gene. Biologically active agents include those especially useful for long-term therapy, such as hormonal treatment, for example contraception and hormone replacement therapy, and for treatment of diseases such as osteoporosis, cancer, epilepsy, Parkinson's disease and pain. The suitable biologically active agents may also comprise anti-inflammatory agents, anti-infective agents (e.g. antibiotics and antiviral agents), anti-microbial, analgesics and analgesic combinations, anti-asthmatic agents, anticonvulsants, antidepressants, anti-diabetic agents, and agents used for other diseases.

In a preferred embodiment of the invention, the article is characterized in that the biologically active compound comprises an anti-microbial agent. In tissue ligation for instance, the incorporation of an anti-microbial agent will help to avoid infections and therefore promote healing. According to another preferred embodiment, the article, and in particular the coating thereof, bears more than one biologically active agent.

The inorganic oxide coating can be tailored to release the biologically active agent or agents composed in it at a controlled rate under in vivo conditions.

A particularly preferred embodiment of the article according to the invention is characterized in that the coating comprises a carrier layer in direct contact with the surface of the structural member. Such a carrier layer can be provided onto the filament(s) of the structural member by a pre-treatment thereof, including by grafting suitable reactive moieties onto the HPPE filament(s), preferably acrylic moieties, by chemical oxidation, by plasma deposition, including atmospheric and vacuum plasma deposition, as well as by other suitable methods. It has turned out that the preferred method of applying a carrier layer to the structural member comprises vacuum plasma deposition. This method in particular allows to bring the reactive moieties into the structural member, i.e. onto the majority of the filaments thereof, without substantially lowering the tenacity of the filaments.

Particularly preferred is an article, wherein the carrier layer comprises a porous layer, comprising carbon atoms. Such a layer is readily produced by plasma deposition, more preferably vacuum plasma deposition. Porosity is preferably created in the carrier layer. In a preferred method, porosity is created by gas etching, a technique known per se. Particularly preferred are $NH_3$— and/or $CO_2$— gas etching to functionalize the surface, since this improves adhesion of the carrier layer to the substrate and/or to the biodegradable coating. M. M. Hossain et al. (Plasma Process. Polym. 2007, 4, 471-481, incorporated herein by reference) describe a technique based on simultaneous plasma polymerization and plasma etching for producing and depositing such porous layer on polyester textiles.

A particular advantageous embodiment of the article is characterized in that the inorganic oxide is substantially incorporated in the (pores) of the carrier layer. It was found that vacuum plasma deposition in particular is beneficial to incorporation of the inorganic oxide in the pores of the carrier layer.

Providing a porous carbon layer by vacuum plasma deposition in combination with sol-gel synthesis of the inorganic oxide of the present invention offers the advantage of mild processing conditions that will not significantly impair the mechanical properties of the HPPE structural member. Also, a high level of control over the resulting structure, particularly as it pertains to porosity and bio-resorbable properties, is another advantage. The structural member of a preferred surgical repair article according to the invention has a tenacity loss relative to a structural member without a carrier coating and/or biodegradable coating of less than 25%, more preferably of less than 10%, and most preferably of less than 5%.

It was found moreover that by combining (vacuum) plasma polymerisation of ethylene gas and gas etching to create porosity in one single process step allows reaching a relatively low total coating layer thickness. Although the relative thickness of the coating with respect to the dimensions of the structural member and/or the HPPE filaments may be varied between wide limits, preferred is a relatively low coating layer thickness. If the coating layer is too thick in relation to the structural member and/or the HPPE filaments, the flexibility of the member and/or the filaments becomes too low, but this will generally be dependent on the use of, and the size or dimensions of the member and/or the filaments.

The smaller sutures typically have a diameter in the range of 20 to 200 micrometer if considered to be virtually round, whereas larger surgical sutures or orthopaedic cables may have diameters of up to 1 or 3 mm, or even higher. In a preferred embodiment of the repair article according to the invention, the mass of the coating is less than 50% of the total mass of the coated filaments, more preferably less than 30%, even more preferably less than 10%, and most preferably less than 5% of the total mass of the coated filaments, such as less than 1% of the total mass of the coated filaments. In a preferred embodiment, the mass of the coating is more than about 0.1% of the coated filaments, and preferably more than about 1% of the total mass of the coated filaments. Higher values are possible particularly if a large biologically active agent is required or a high loading of the biologically active component is required. The mass of the coating is defined as the mass of the coating in its final (dried) state, i.e. after substantial removal of the solvent of the sol/gel process, and includes the mass of the biodegradable coating and the carrier coating, if applicable. The relatively small amount of coating in the most preferred embodiments keeps the filaments flexible, and moreover improves the coating's integrity. This is important, since premature release of the biologically active agent by breakage of the coating when handling the repair article for instance, is undesirable. For most applications, an article according to the invention preferably comprises a coating having a thickness of at most 100 nm, more preferably at most 80 nm, and even more preferably at most 60 nm. A coating thickness of at least 1 nm, and preferably at least 5 nm such as at least 20 nm is preferred to maintain a high flexibility of the coated article while keeping the risk of mechanical failure low. In a particularly preferred embodiment of the repair article, the coating has a thickness of between 1 and 50 nm and/or the filaments have a linear density of about 0.3 to about 10 dtex per filament. This embodiment provides an optimum between flexibility and handleability of the article, and coating integrity. The thickness of the total coating is defined as the thickness of the biodegradable coating and the carrier coating, if applicable. In the latter embodiment, part of the biodegradable coating may be incorporated in the pores of the carrier layer.

Very thick coatings may for example be advantageous when the surgical repair product comprises thick monofilament or monofilament-like yarn for example having a diameter of about 50 to 250 μm. In this case thick coatings having a thickness of for example 100 nm to 10 μm may be advantageous. Such thick coatings have the advantage that very high loadings of biologically active compound may be achieved as well as very large molecules, such as for example growth factors, antibiotics, etc, easily may be incorporated in the coating.

The coating of the article according to the invention may cover the structural member as a whole; that is may form a sheath around the structural member. The coating may also substantially cover the total surface of the filaments, thus increasing the aerial surface of the coating, and therefore also the area of interaction of the biologically active agent with the physiological surroundings. Even when using the small amounts of the preferred embodiments described above, it appeared possible to substantially cover the total surface of the filaments.

Preferably, the space between the filaments of the structural member is not or only little filled; that is most of the filaments can move or shift relative to each other, or be separated from each other. This can for example be examined after cutting the structural member open in the length direction. The advantage hereof is that the flexibility of the structural member remains favourable, also for members of larger diameter (or suture size), such as multifilaments. The surgical repair article according to the invention shows high tensile strength or tenacity, and preferably has a tenacity of at least 10 cN/dtex, more preferably of at least 15, 20, 25, 28 cN/dtex, or even more than 30 or 40 cN/dtex.

In yet another embodiment of the invention, the surgical repair article is a tape or a film, and the HPPE is comprised in the tape or film. The tape or film is here considered a monofilament of HPPE even if the tape or film may have a size and shape much larger than monofilaments typically used in a multifilament HPPE yarn as it is extruded from a melt or solution through one spin hole, which spin hole may be quite large and for example rectangular). Such a tape or film may for example be produced by feeding a polyethylene, preferably an ultra high molecular weight polyethylene, to an extruder, extruding a tape or a film at a temperature above the melting point of HPPE and drawing the extruded polymeric tape or film unidirectionally or biaxially. If desired, prior to feeding the polyethylene to the extruder, the polyethylene may be mixed with a suitable liquid organic compound such as for example decaline or paraffin, for instance to form a solution, a suspension or a gel, such as is preferably the case when using UHMWPE. In one sub-embodiment of this embodiment of the invention, the surgical repair article is a porous membrane, preferably a porous HPPE membrane, which membrane for example may be prepared according to EP 500 173 or EP 504 954 (both incorporated herein by reference) and subsequently coated with a coating comprising a sol/gel as described elsewhere.

Another way for producing tapes or films is via a solid state process comprising the steps of calendaring powdered HPPE at elevated temperature to form a coherent tape or film, followed by stretching the tape or film unidirectionally or biaxially.

In another embodiment the article is an orthopaedic cable, very suitable to be used for holding together bone parts for instance.

The invention further specifically relates to the use of a structural member as defined and described above in various embodiments, for making a surgical repair article having an advantageous combination of a.o. high tensile strength, controlled release properties and biocompatibility.

Preferably, the surgical repair article according to the invention comprises a mesh, a fabric, a surgical suture, and/or a medical cable. Medical cables include but are not limited to orthopaedic cables, sternum closure cables, and the like. The invention also relates to a kit of parts containing such a medical cable and a fixing member for use in surgery. In another preferred embodiment, the invention relates to a kit of parts containing such a surgical suture and a surgical needle for use in surgery. In yet another preferred embodiment, the invention relates to a kit of parts containing such a surgical suture and an anchor for use in surgery.

The article of the invention is particularly useful in a method of surgical treatment.

The invention further relates to a method of making a surgical repair article according to the invention, the method comprising the steps of preparing a solution of precursor molecules of an inorganic oxide in a suitable solvent, hydrolysing the solution, coating a precursor structural member, which may or may not already comprise a carrier coating, and contains HPPE monofilament or multifilaments with the thus obtained hydrolysed solution, and heat treating the coated filaments at a suitable temperature to form a sol/gel coating of the inorganic oxide onto the surface of the structural member and/or the surface of the filaments.

The structure of a precursor member for applying in the method according to the invention is not particularly critical. Suitable constructions of HPPE filaments include twisted multifilament yarns, or braided, woven or knitted constructions, or a hybrid construction. Preferably a braided precursor is used, since this has more initial coherence and is easier to handle. Suitable braided precursors include circular or tubular braids, but also spiroid braid or flat braid constructions can be applied. In general, for making relatively thin repair articles a simple precursor construction is preferred, whereas for thicker articles more complicated constructions, like kernmantle (twisted filaments in core-braided sheath), or braid-on-braid (also called double braided) cords, can be applied.

In the method, the sol-gel derived inorganic oxide coating is preferably prepared from a solution comprising water, precursor molecules of an alkoxide or inorganic silicate, and a lower alcohol as solvent, such as for instance ethanol. An acid or a base is used as a catalyst, and said sol is dried, after the coating step.

Typically an alkoxide, and preferably tetraethoxysilane (TEOS) is used for preparing the sol-gel derived inorganic oxide coating. If an inorganic silicate is used for preparing the sol-gel derived $SiO_2$, it is preferably sodium or potassium silicate. The lower alcohol is preferably ethanol. In order to influence the properties of the sol/gel coating, the composition of the sol can be modified. The modifications are preferably directed to adding other precursors, preferably silanes provided with pendant groups to improve flexibility, changing the water content, changing the alkoxide or inorganic silicate content, changing the amount of alcohol, adjusting pH by adding an acid or base, for which purpose preferably the acid or base used as the catalyst is employed, changing the type of precursor, and modifying the amount of bioactive agent, optionally added to the solution, modifying the molar ratio of water to the alkoxide or inorganic silicate, and/or molar ratio of alcohol to the alkoxide or inorganic silicate, and any combination thereof.

In a preferred method according to the invention, the solution of the precursor molecules comprises less than 20% by mass of precursor molecules. The ensuing coating thickness can in this case be relatively small, in the order of 50-100 nanometers, which provides advantages. Indeed, such embodiment of the coating does not easily break or chip of from the structural member, and the flexibility of the repair article is not impaired much.

The starting pH of the solution can be selected within a wide range, but it has advantages when the starting pH is from 0.5 to 12.0, preferably from 3.5 to 5.0, most preferably about 4.0. To obtain the best results, the molar ratio of water to the alkoxide or inorganic silicate is selected between 0.5 and 10, and preferably between 1.5 and 7.5. The molar ratio of alcohol to the alkoxide or inorganic silicate can be chosen within wide ranges, but is preferably more than 10, and more preferably larger than 100, even more preferably larger than 200, even more preferably larger than 400, and most preferably selected between 10-500.

Coating a precursor structural member containing a plurality of HPPE filaments with the thus obtained hydrolysed solution can be carried out by any method known in the art, such as for example dip-coating or spray-coating. The final thickness of the inorganic oxide sol-gel coating can be controlled and optimised by diluting the solution, specifically by adding more solvent (typically ethanol) to the solution. Sol-gel coating thickness can also be adjusted by changing the spin-coating or dip-coating rate, or by changing the application rate of the coating, or both.

In certain embodiments according to the present invention patterning techniques to template the sol-gel coating composition at multiple length-scales can be used. Sacrificial porogens may also be used to pattern the deposition of the sol-gel composition coating onto the structural member, comprising HPPE filaments. This would allow thicker coating layers without compromising bending performance.

Drying of the solution, preferably after the coating step, can be performed by heat treatment according to a number of methods. Drying by ambient heat, vacuum drying, electromagnetic drying, acoustic drying, spray-drying or freeze-drying may all be used. In a preferred embodiment of the method, the heat treatment temperature is below 130° C., more preferably below 80° C., even more preferably below 50° C., most preferably room temperature. These preferred temperature conditions are selected such that the HPPE filaments of the structural member will not soften or start to melt, so that they do not loose their molecular orientation. Residence times during which the precursor structural member and coating are exposed to the oven temperature are for example within the range from about 30 seconds to about 15 min. In a special embodiment of the invention, the monofilaments are kept under tension by drawing them during heat exposure, preferably with a draw ratio of about 1.0 to 2.5, more preferably of about 1.0 to 1.2. The thickness of the coating being formed can be controlled by increasing or decreasing the temperature, and/or by increasing or decreasing the residence time. The skilled man can find favourable settings by routine experimentation. After drying, the coated structural member obtained preferably contains less than 800 ppm of solvent, more preferably less than 500, 250, or even less than 100 ppm.

According to the invention, the method for producing a surgical repair article comprises the step of incorporating a biologically active compound, like a medical drug into the article, preferably into the coating thereof. Another way to incorporate a medical drug into the member is to add the medical drug to the solvent before the heat treatment step, but also other routes are possible. A biologically active agent or agents can also be added to the sol before gel formation, which is the preferred route. The biologically active agent or agents can be any agent inducing a biological response in a living tissue, organ or organism as defined and exemplified above.

According to the invention, the surgical repair article is capable of sustained, controlled and time-release bioactive material delivery. The desired combination of relatively fast dissolution rates of the coating to release the bioactive agent and expose the biocompatible HPPE structural member underneath is achieved by the preferred embodiments of the method, as described above. Delivery (release) of a bioactive material may start upon implantation of the surgical repair article, or at a particular time after implantation, and preferably the delivery rate follows a bell shaped curve over time, with an initially slow but exponentially increasing delivery rate rising to a maximal rate and wherein the rate then exponentially decreases over time, finally tailing off to zero. In the field of sustained-release bioactive material delivery it is generally considered desirable to avoid a large bioactive material delivery "burst" wherein the majority of the bioactive material is delivered in a short amount of time. This preferred delivery profile is achieved by providing a coating according to the invention on a HPPE structural member.

In yet another embodiment, the invention provides for the use of the surgical repair article of the present invention for medical applications. Exemplary medical applications include, but are not limited to joint arthroplasty, orthopedic and spine implants for example meniscus implants, surgical sutures, meshes for example hernia meshes, fabrics, woven or non-woven sheets, tapes, ribbons, bands, artificial joints, cables such as trauma fixation cables, sternum closure cables, prophylactic or per prosthetic cables, long bone fracture fixation cables, small bone fracture fixation cables, tube-like products for e.g. ligament replacement, endless loop products, bag-like, balloon-like products.

EXAMPLES

Anti-Microbial Activity

Examples 1 and 2

Anti-microbial activity of various $SiO_2$-triclosan coatings according to the invention. The simultaneous RF plasma polymerization and gas etching of the Dyneema Purity® braids were carried out at EMPA (Swiss Materials Science & Technology, Lerchenfeldstrasse 5, CH-9014, St. Gallen, Switzerland).

Example 1

Coating of HPPE Sutures $SiO_2$-triclosan coating formulations were prepared by dissolving 50 g/L hydrolyzed TEOS in ethanol with respectively 0.02, 0.04 and 0.08 g/L triclosan. HPPE braids (Dyneema Purity@ braids (16×1×110)) were pretreated by combining vacuum plasma polymerization and gas etching (C:H:N or C:H:O treatment). $SiO_2$-triclosan coating was subsequently applied by dip coating the pretreated braids in the $SiO_2$-triclosan coating formulation. The solvent of the coating formulation, i.e. ethanol, was thereafter evaporated at 50° C. (for 10 min) whereby $SiO_2$-triclosan coated HPPE sutures with a coating thickness of approximately 10 nm thickness were obtained.

Example 2 (a)-(e)

Anti-Microbial Activity Testing

*Escherichia coli* ATCC 11105 was cultured from frozen stock in sterile Luria Bettani medium. The bacterial suspension had a concentration of about 109 CFU/mL.

LB agar plates were inoculated with 100 pL of this bacterial suspension. The sutures prepared in Example 1 were cut into approximate 5 cm lengths; straight sections of suture were used. Each suture was pressed in the agar with sterile forceps to optimize contact with the agar surface. The agar plates were subsequently incubated at 37° C. for 24 h in an exicator filled with a saturated salt solution to prevent dehydration of the agar.

The width of the zone of growth inhibition at right angles to the suture length was recorded to nearest 1 mm at three spots along the suture and photographic images of the agar plates were generated.

Figure 1:
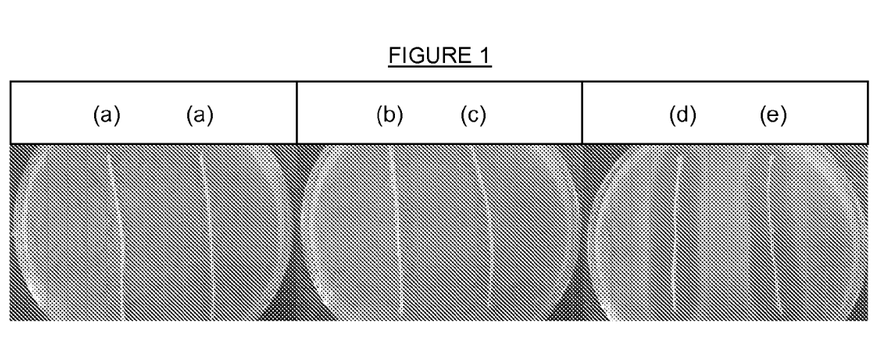
FIG. 1 shows zones of inhibition in Example 2.

In FIG. 1, zones of inhibition testing of (a) untreated HPPE braid, (b) C:H:N pretreated HPPE braid without coating, (c) C:H:O pretreated HPPE braid without coating, (d) C:H:N pretreated and $SiO_2$-triclosan coated (0.02 g/L triclosan) HPPE braid, (e) C:H:O pretreated and $SiO_2$-triclosan coated (0.02 g/L triclosan) HPPE braid.

In FIG. 1, it is observed that the growth of the tested *E. coli* strain is not inhibited by the untreated HPPE braid (Example 2 (a)), nor by the C:H:N and C:H:O pretreated HPPE braids (Example 2 (b) and (c)). The application of the silicon dioxide-triclosan coating (Example 2 (d) and (e)), on the contrary, results in a significant anti-microbial activity of the braid.

Example 3 (A)-(F)

Extended Antimicrobial Activity

The development of inhibition zones over time for various antimicrobial coatings according to the invention was investigated in Example 3.

A number of HPPE braids (Dyneema Purity® braids (16×1×110)) was coated as described in Example 1. Table 1 shows the widths of the growth inhibition zones obtained for the C:H:N or C:H:O pretreated Dyneema Purity® braids coated with the hydrolyzed TEOS formulations of different triclosan content (0.02, 0.04 and 0.08 g/L). Anti-microbial activity testing was performed for freshly coated braids and for coated braids previously incubated in uninoculated agar for 8 days.

Samples

3A: C:H:N pretreated HPPE braid coated with $SiO_2$-triclosan (0.02 g/L triclosan)

3B: C:H:O pretreated HPPE braid coated with $SiO_2$-triclosan (0.02 g/L triclosan)

3C: C:H:N pretreated HPPE braid coated with $SiO_2$-triclosan (0.04 g/L triclosan)

3D: C:H:O pretreated HPPE braid coated with $SiO_2$-triclosan (0.04 g/L triclosan)

3E: C:H:N pretreated HPPE braid coated with SiO$_2$-triclosan (0.08 g/L triclosan)

3F: C:H:O pretreated HPPE coated with SiO$_2$-triclosan (0.08 g/L triclosan)

TABLE 1

Size of growth inhibition zone (mm)

| Sample | Prior incubation time in uninoculated agar (days) | |
|---|---|---|
| | 0 | 8 |
| 3A | 17 | 4 |
| 3B | 18 | 5 |
| 3C | 19 | 8 |
| 3D | 19 | 9 |
| 3E | 21 | 11 |
| 3F | 22 | 11 |

From Table 1 it is clear that all coated samples are antimicrobial active against the tested *E. coli* strain, even after 8 days of incubation in agar prior to the testing. Slightly larger inhibition zones are found for coatings with larger triclosan content. The observed differences become more pronounced for the coatings previously incubated in the agar for 8 days. When the coated braids are kept in the inoculated agar at 37° C. after the zone of inhibition testing, they remain free of bacteria for at least 3.5 months (longer testing was not possible due to the reduced quality of the agar with time).

Example 4

Coating Degradation

Coatings of approximately 70 nm thickness were obtained by spincoating glass plates at 400 rpm with 40 g/L hydrolysed TEOS solutions in ethanol. Coatings of different density were prepared by evaporating the solvent of the coating formulation, i.e. ethanol, at different temperatures, i.e. 50 and 100° C., after coating application.

The different coatings were incubated in phosphate buffered saline (PBS) solution at 37° C. to mimic in vivo conditions. The dissolution of the coatings was monitored by recording the silicium release in the PBS buffer. Silicium quantification was performed by means of atomic absorption spectrophotometry. Uncoated glass plates were used as reference.

Figure 2:
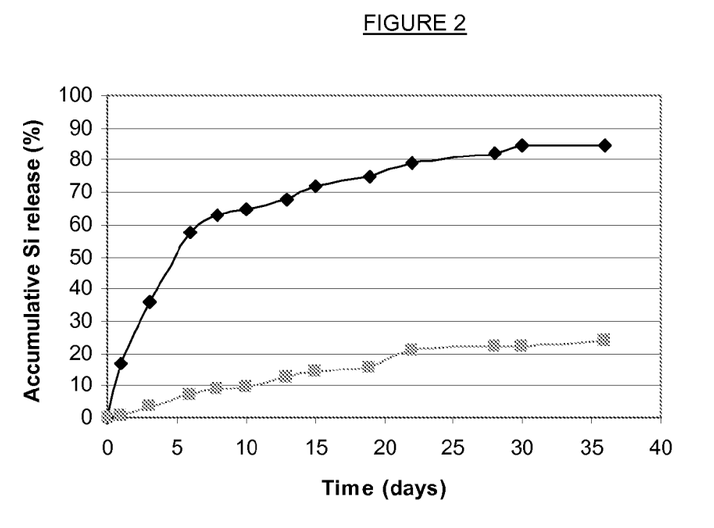
FIG. 2 shows dissolution of different $SiO_2$ coatings according to the invention.

In FIG. 2, the accumulative silicium release in phosphate buffered saline solution at 37° C. from 70 nm thick silicium dioxide coatings on glass plates, cured at (♦) 50° C. and (▪) 100° C. for 5 min after coating application is shown.

It is observed that the coating cured at 100° C. is much more stable in the PBS buffer at 37° C. than the coating cured at 50° C. Approximately 85% of the coating cured at 50° C. is degraded after 36 days in PBS buffer at 37° C., compared to only 24% of the coating cured at 100° C. A higher stability was expected for the coating cured at 100° C. since curing at higher temperature results in a more dense network.

The release of a biologically active agents such as an antimicrobial agent (e.g. triclosan) or a growth factor is controlled by a combination of diffusion through the coating of the active agent (mainly dependent on size of the active agent and the openness of the coating) and release of the active agent due to degradation of the coating as observed in FIG. 2. From Example 4 it is clear that coatings with a wide range of degradation profiles can be obtained by changing the curing temperature of the coating. This proves that the invention provides a means to control release of active component for the coatings and coated surgical repair products according to the invention by engineering the coating according to the desired release profile.

Example 5

Coating Appearance and Adhesion

Scanning Electron Microscopy (SEM) analysis was used to assess the adhesion of:

i) a SiO$_2$ coating on a HPPE yarn (Dyneema Purity@ yarn (220 dTex SGX; 2 dpf) and ii) a SiO$_2$ coating on a pretreated (C:H:O treatment) HPPE yarn (Dyneema Purity@ yarn (220 dTex SGX; 2 dpf).

The HPPE yarn of i) is herein after referred to as HHPE yarn SiO$_2$ and the HPPE yarn of ii) is herein referred to as HHPE yarn CHO/SiO$_2$.

The HPPE yarn SiO$_2$ was prepared as follows: SiO$_2$ coatings of approximately 10 nm thickness were subsequently applied by dip coating the pretreated yarn in a 50 g/L hydrolyzed TEOS solution in ethanol containing 5.6 g/L Basonyl Violet to stain the coating. The solvent of the coating formulation, i.e. ethanol, was evaporated at 50° C. (for 10 min) after coating application.

The HPPE yarn CHO/SiO$_2$ was prepared as follows:

HPPE yarn (Dyneema Purity@ yarn (220 dTex SGX; 2 dpf) was pretreated by combining vacuum plasma polymerization and gas etching (C:H:O treatment). SiO$_2$ coatings of approximately 10 nm thickness were subsequently applied by dip coating the pretreated yarn in a 50 g/L hydrolyzed TEOS solution in ethanol containing 5.6 g/L Basonyl Violet to stain the coating. The solvent of the coating formulation, i.e. ethanol, was evaporated at 50° C. (for 10 min) after coating application.

The aforementioned HPPE yarns, namely HPPE yarn SiO$_2$ and HPPE yarn CHO/SiO$_2$ once prepared, they were fixed with double sided adhesive tape to a SEM aluminum sample holder and coated with a conductive Au/Pd layer.

In order to study the adhesion of the coating to the pretreated Dyneema Purity® yarn, the coated yarn was pressed to the adhesive tape with a glass plate (2×5 cm). Then, the yarn was peeled off from the tape and glued upside down to the tape on the same SEM sample holder. The yarn was rotated 90° to allow investigation of the parts of coating that remained on the tape after peeling off the coated yarn. Imaging was done using a Philips CPSEM XL30 at an acceleration voltage of 10 kV. Imaging of the aforementioned HPPE yarns was performed:

i) prior to the peel off of the yarn from the double-sided adhesion tape and ii) after the peel off of the yarn from the double-sided adhesion tape.

For simplicity, step ii) above is referred to hereinafter as "adhesion test".

Figure 3:
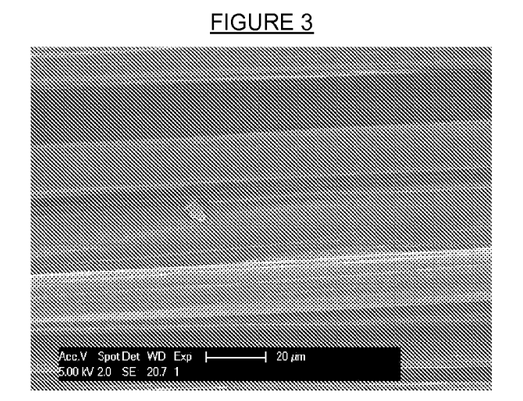
FIG. 3 shows SEM image of C:H:O pretreated HPPE yarn coated with a $SiO_2$ layer.

FIG. 3 shows the appearance of the stained silicon dioxide coating on the HPPE yarn CHO/SiO$_2$ prior to the adhesion testing. A uniform coating was observed.

Figure 4:
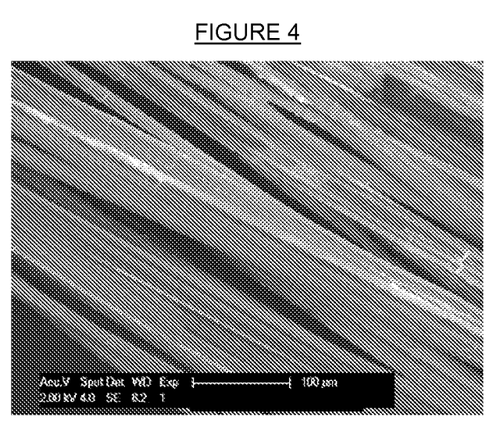
FIG. 4 shows SEM image of C:H:O pretreated HPPE yarn coated with a $SiO_2$ layer after pealing (adhesion test)

FIG. 4 shows the HPPE yarn CHO/SiO$_2$ yarn after the adhesion test.

Figure 5:
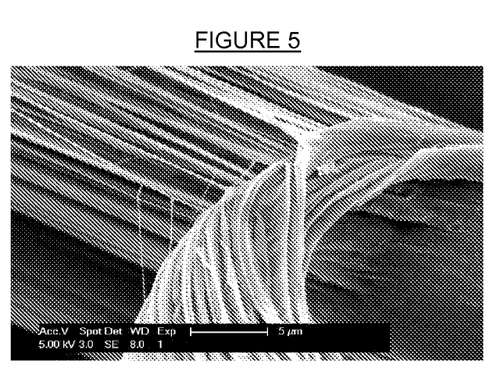
FIG. 5 shows SEM image of C:H:O pretreated HPPE yarn coated with a $SiO_2$ layer after pealing. (adhesion test)
Figure 6:
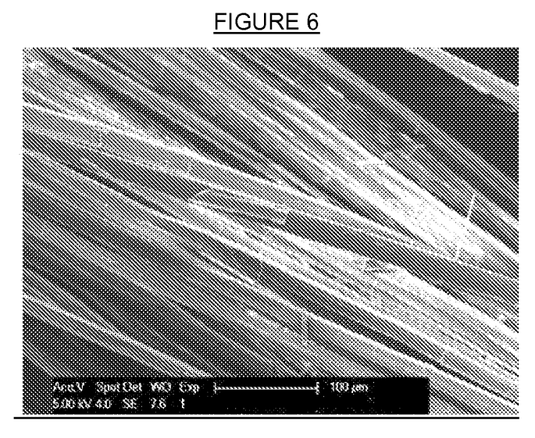
FIG. 6 shows SEM image of HPPE yarn coated with a $SiO_2$ layer after pealing (adhesion test)

FIG. 5 is a magnification of FIG. 4 showing the HPPE yarn CHO/SiO$_2$ yarn after the adhesion test the pretreated and coated yarn after the adhesion testing. FIG. 6 shows the HPPE yarn SiO$_2$ yarn after the adhesion test.

Figure 7:
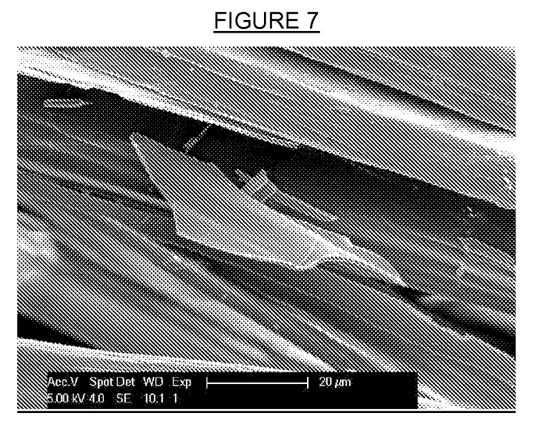
FIG. 7 shows SEM image of HPPE yarn coated with a $SiO_2$ layer after pealing (adhesion test).

FIG. 7 is a magnification of FIG. 6 showing the HPPE yarn SiO$_2$ yarn after the adhesion test. From FIG. 4 and FIG. 5, it can be clearly observed that the SiO$_2$ coating remains on the yarn after the adhesion testing. No loose coating parts were found on the tape after peeling off the coated yarn (not shown). The polyethylene fibrils become visible after peeling the coated yarn from the tape. This shows that the adhesion of the $SiO_2$ coating to the Dyneema Purity® yarn is stronger than the tensile strength of the Dyneema Purity® yarn in the direction of the peel-off test. It is highly surprising that such a strong bonding was obtained between the $SiO_2$ coating and the HPPE, as HPPE is usually considered very hard to coat due to the inherent slippery nature of the polyethylene. This is further emphasized by the surprising fact that the integrity of the bond between the coating and the HPPE remained intact after the very harsh bending of the yarn during the testing.

Upon comparing FIG. 4 (HPPE yarn CHO/$SiO_2$ yarn) with FIG. 6 (HPPE yarn $SiO_2$ yarn) and in particular the magnifications of FIG. 4 with FIG. 6, that are shown FIG. 5 (HPPE yarn CHO/$SiO_2$ yarn) and FIG. 7 (HPPE yarn $SiO_2$ yarn), respectively, it is clear that the adhesion of the $SiO_2$ coating was surprisingly improved due to the C:H:O pretreatment of the HPPE yarn. As it can be also seen upon comparing FIG. 5 with FIG. 7, this adhesion improvement of the $SiO_2$ coating to an HPPE yarn was very significant since in the case of the HPPE yarn CHO/$SiO_2$ yarn after the adhesion test (FIG. 5), the fibrils of HPPE were visible without at the same time the $SiO_2$ coating to have been peeled off. This is a clear indication of a substrate failure (HPPE) rather than a coating ($SiO_2$) failure as a result of the adhesion test. In contrast to that, when a HPPE yarn was not subjected to a C:H:O treatment, the $SiO_2$ coating failed before the substrate (HPPE) failed (see FIG. 7, where pieces of $SiO_2$ coating were visible to have been peeled-off as a result of the adhesion test).

The invention claimed is:

1. A surgical repair article, comprising:
   a structural member of high performance polyethylene (HPPE) filaments, and
   a biodegradable coating applied to the surface of the structural member, wherein the biodegradable coating comprises a porous carrier layer applied to the surface of the structural member by plasma deposition, a sol/gel produced inorganic oxide and a biologically active compound incorporated therein.

2. The article according to claim 1, wherein the high performance polyethylene comprises ultra-high molar mass polyethylene (UHMWPE).

3. The article according to claim 1, wherein the inorganic oxide is selected from the group consisting of silicon oxides, aluminum oxides, titanium oxides and zirconium oxides.

4. The article according to claim 1, wherein the biologically active compound comprises at least one selected from the group consisting of an anti-microbial agent and a growth factor.

5. The article according to claim 1, wherein the carrier layer is applied to the surface of the structural member by vacuum plasma deposition.

6. The article according to claim 1, wherein the inorganic oxide is incorporated in the carrier layer.

7. The article according to claim 1, having a tenacity loss relative to a structural member without a carrier coating and/or biodegradable coating of less than 10%.

8. The article to claim 1, wherein the coating has a mass which is less than 50% of a total mass of coated filaments comprised of the filaments coated with the coating.

9. The article according to claim 1, wherein the coating has a total thickness of between 1 nm and 10 μm.

10. The article according to claim 1, wherein the coating covers substantially the entire surface of the filaments.

11. The article according to claim 1, wherein the article is selected from the group consisting of a mesh, a fabric, a surgical suture, and a medical cable.

12. The article according to claim 1, wherein the inorganic oxide is a silicon oxide.

13. The article according to claim 8, wherein the coating has a mass which is less than 30% of the total mass of the coated filaments.

14. The article according to claim 8, wherein the coating has a mass which is less than 10% of the total mass of the coated filaments.

15. The article according to claim 8, wherein the coating has a mass which is less than 10% of the total mass of the coated filaments.

16. The article according to claim 8, wherein the coating has a mass which is less than 5% of the total mass of the coated filaments.

17. The article according to claim 8, wherein the coating has a mass which is less than 1% of the total mass of the coated filaments.

18. The article according to claim 9, wherein the coating has a total thickness of between 5 nm and 100 nm.

19. The article according to claim 9, wherein the coating has a total thickness of between 10 nm and 80 nm.

20. The article according to claim 9, wherein the coating has a total thickness of between 20 nm and 60 nm.

21. A kit of parts containing a medical cable according to claim 11 and a fixing member for use in surgery.

22. A method of making a surgical repair article according to claim 1, comprising the steps of:
   (a) forming a porous carrier layer by plasma deposition on surfaces of a precursor structural member containing the HPPE filaments,
   (b) preparing a solution of precursor molecules of an inorganic oxide in a suitable solvent,
   (c) hydrolyzing the solution of step (b),
   (d) coating the precursor structural member containing the HPPE filaments with the hydrolyzed solution of step (c), and
   (e) heat-treating the precursor structural member at a heat treatment temperature to form a sol/gel coating of the inorganic oxide onto the surface of the structural member.

23. The method according to claim 22, wherein the heat treatment temperature of step (d) is below 130° C.

24. The method according to claim 23, wherein the heat treatment temperature of step (d) is below 50° C.

25. The method according to claim 23, wherein the heat treatment temperature of step (d) is about room temperature.

26. The method according to claim 22, wherein the solution of the precursor molecules comprises less than 20% by mass of the precursor molecules.

27. The method according to claim 22, wherein the HPPE filaments comprise UHMWPE filaments having a tensile strength of more than 2.0 GPa.

28. The method according to claim 22, wherein the HPPE filaments have a linear density of about 0.3 to about 10 dtex per filament.

* * * * *